United States Patent [19]

Foley et al.

[11] Patent Number: 5,779,654
[45] Date of Patent: Jul. 14, 1998

[54] CLEAN BREATH WAND

[76] Inventors: Rita S. Foley; Patrick F. Foley, both of 1214 Eric La., Lake Zurich, Ill. 60047

[21] Appl. No.: 824,502

[22] Filed: Mar. 26, 1997

[51] Int. Cl.$^6$ ........................................ A61M 7/00
[52] U.S. Cl. .................. 601/137; 601/136; 601/159; 601/160; 601/155; 606/161
[58] Field of Search .................. 606/161; 601/17, 601/136, 137, 138, 139, 154, 155, 159, 160

[56] References Cited

U.S. PATENT DOCUMENTS

| | | | |
|---|---|---|---|
| 619,466 | 2/1899 | Buchmann | 601/161 |
| 1,851,396 | 3/1932 | Mabry | 601/161 |
| 2,218,072 | 10/1940 | Runnels | 601/161 |
| 2,583,750 | 1/1952 | Runnels | 601/161 |
| 4,488,327 | 12/1984 | Snider | 15/111 |
| 4,787,845 | 11/1988 | Valentine | 433/88 |
| 4,958,751 | 9/1990 | Curtis et al. | 222/192 |
| 4,973,250 | 11/1990 | Milman | 433/215 |
| 4,979,504 | 12/1990 | Mills | 128/66 |
| 5,127,831 | 7/1992 | Bab | 433/80 |
| 5,217,475 | 6/1993 | Kuber | 606/161 |
| 5,218,956 | 6/1993 | Handler et al. | 128/66 |
| 5,558,518 | 9/1996 | Bab et al. | 433/80 |
| 5,569,278 | 10/1996 | Persad | 606/161 |

FOREIGN PATENT DOCUMENTS

| | | | |
|---|---|---|---|
| 659404 | 6/1929 | France | 601/161 |

*Primary Examiner*—Robert A. Hafer
*Assistant Examiner*—Benjamin K. Koo
*Attorney, Agent, or Firm*—Thomas R. Vigil

[57] ABSTRACT

The clean breath wand comprises an elongate hollow body having a distal end, a proximal end and a proximal handle portion, a coupling member for coupling the proximal end to a source of liquid, a head end fixed to the distal end of the hollow body, and the head end having an outer end face with at least one tongue scraping rib or blade thereon and at least one irrigating opening extending through the front end and opening onto the outer end face.

18 Claims, 3 Drawing Sheets

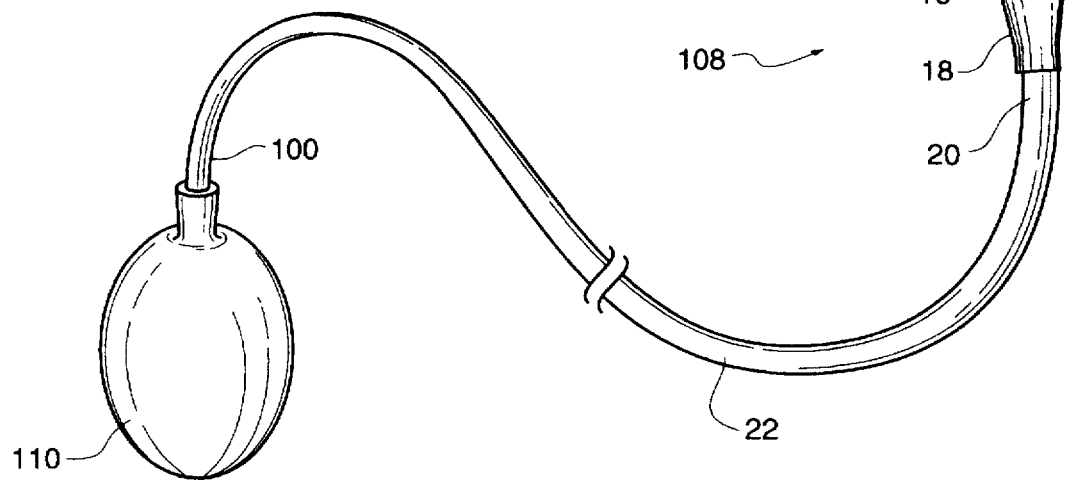
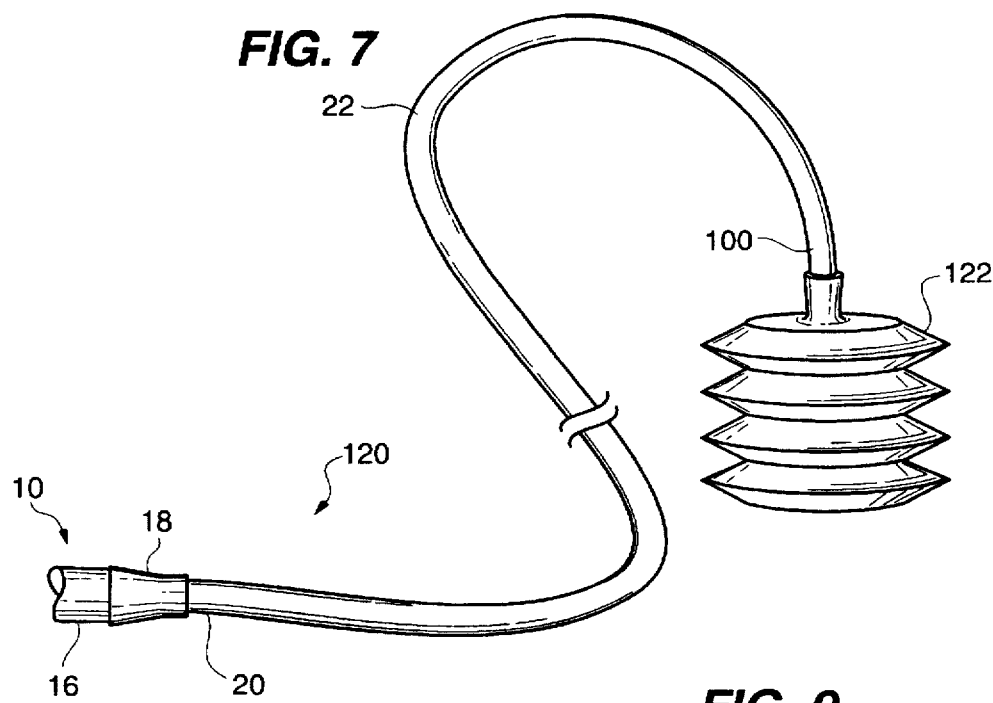
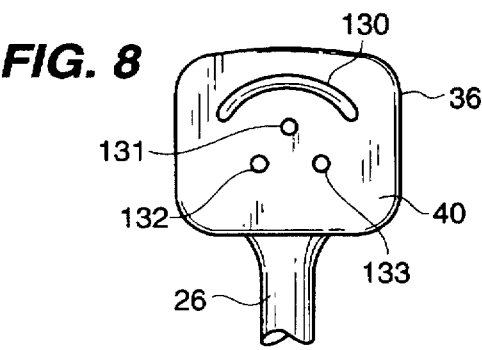
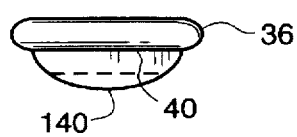
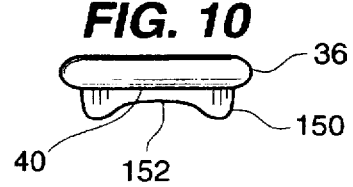

5,779,654

1

CLEAN BREATH WAND

BACKGROUND OF THE INVENTION

1. Field of the Invention

The present invention relates to a clean breath wand comprising a combined tongue scraper and liquid flushing or irrigation system.

2. Description of the Related Art Including Information Disclosed Under 37 CFR §§ 1.97–1.99.

Heretofore a number of oral irrigators have been proposed for irrigating the mouth and particularly the area around the teeth. Examples of such prior art oral irrigators are disclosed in the following U.S. Pat. Nos.:

| U.S. Pat. No. | Patentee |
| --- | --- |
| 5,558,518 | Bab et al. |
| 5,218,956 | Handler et al. |
| 5,127,831 | Bab |
| 4,979,504 | Mills |
| 4,973,250 | Milman |
| 4,958,751 | Curtis et al. |
| 4,787,845 | Valentine |

Also, heretofore a number of tongue scraping devices have been proposed and several examples of same are disclosed in the following U.S. Pat. Nos.:

| U.S. Pat. No. | Patentee |
| --- | --- |
| 5,569,278 | Persad |
| 5,217,475 | Kuber |
| 4,488,327 | Snider |

However, a combined tongue scraper and oral irrigator for washing or flushing the tongue while scraping same thereby to minimize and reduce bad breath or halitosis has not heretofore been proposed.

SUMMARY OF THE INVENTION

According to the present invention there is provided a clean breath wand comprising an elongate hollow body having a distal end, a proximal end and a proximal handle portion, a coupling member for coupling the proximal handle portion to a source of liquid which is pressurized or capable of being placed under pressure, a head end fixed to the distal end of the hollow body, and the head end having an upper distal end, a lower proximal end and an outer end face, at least one irrigating opening fluidly coupled to the hollow interior of the handle portion, extending through the front end adjacent the proximal end and opening onto the outer end face, at least one tongue scraping rib or blade thereon on the outer end face, extending transversely of the outer end face with at least the ends of the at least one rib being curved or inclined toward the elongate hollow body (FIG. 8) and being located above the at least one opening and adjacent the distal end so that the rib prevents pressurized liquid from being directed posteriorly toward a users throat and liquid flow valve means for controlling the delivery of pressurized liquid to the at least one opening.

2

Figure 1:
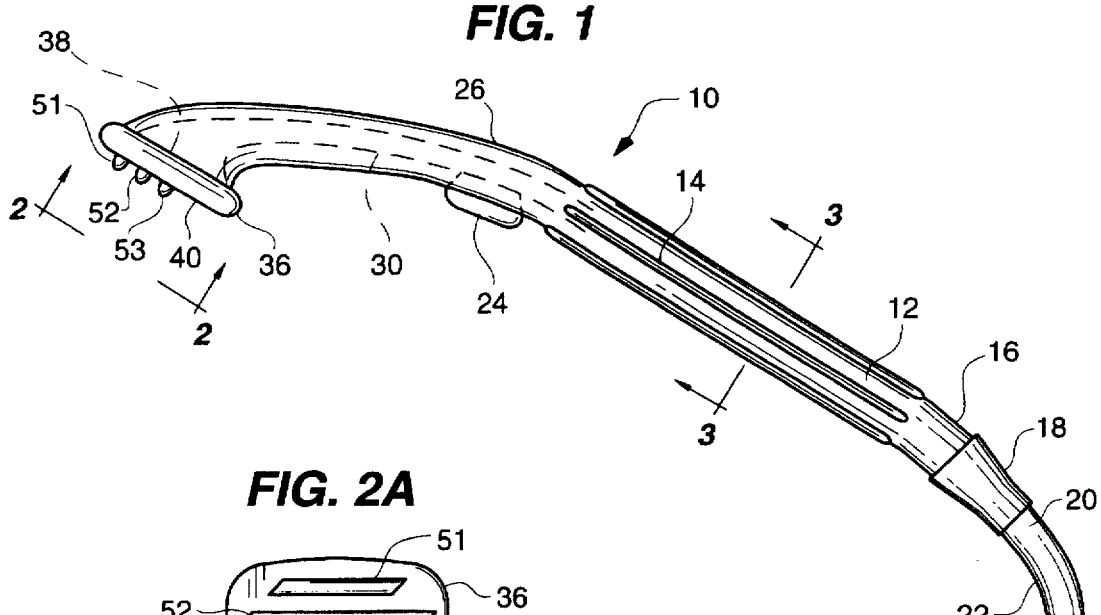
FIG. 1 is a side elevational view of a clean breath wand constructed according to the teachings of the present invention.

FIGS. 2A–2E are a front end view of various shapes or configurations of a front end face of the clean breath wand shown in FIG. 1 and are taken along line 2—2 of FIG. 1.

Figure 3:
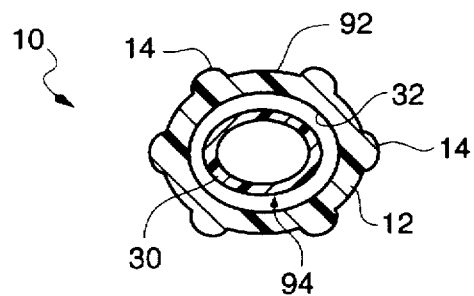

FIG. 3 is a sectional view of a handle portion of the clean breath wand and is taken along line 3—3 of FIG. 1.

Figure 4:
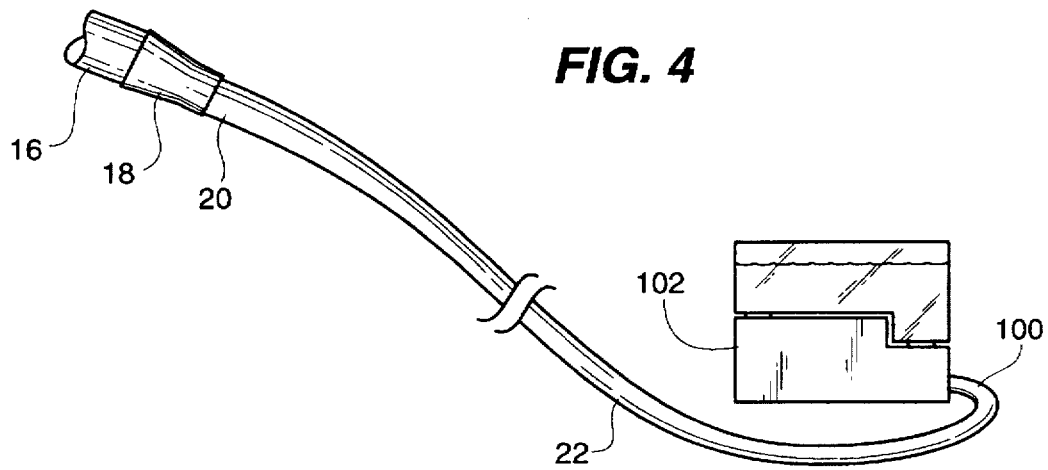

FIG. 4 is a side elevational view with portions broken away of the connection of a proximal end of the clean breath wand to a distal end of a hose leading to an oral irrigator mechanism commonly known as an oral irrigator.

Figure 5:
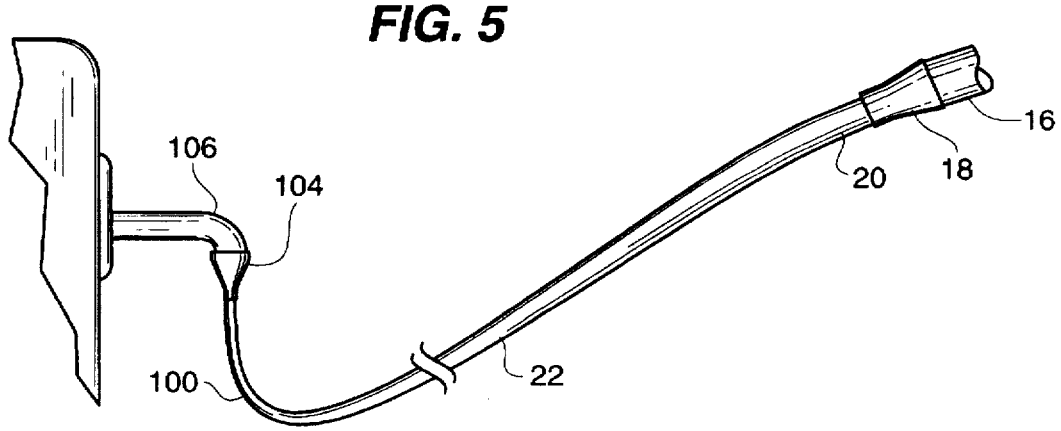

FIG. 5 is a fragmentary side elevational view of a hose having one end connected to the proximal end of the wand and having an adapter at its other end for connection to a faucet.

FIG. 6 is a fragmentary side elevational view of the proximal end of the clean breath wand coupled to a distal end of a hose having at its proximal end connected to a squeeze bulb.

FIG. 7 is a fragmentary side elevational view of the proximal end of the clean breath wand coupled to a distal end of a hose and having at its proximal end a bellows shaped bladder.

Figure 2A:
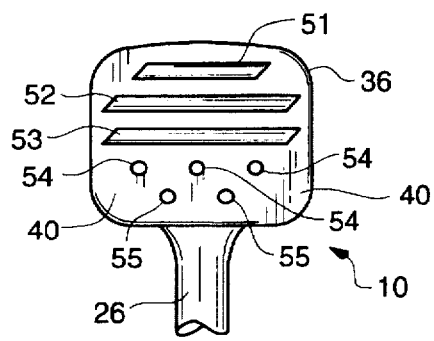

FIG. 8 is a front end view of another configuration of a front end face of the head end of the clean breath wand and is similar to the view shown in FIG. 2A.

FIG. 9 is a top end elevational view of another embodiment of a head end similar to the head end shown in FIG. 1, but showing another form of scraping blade.

FIG. 10 is a top end elevational view of still another embodiment of a head end similar to the head end shown in FIG. 9, but showing still another form of scraping blade.

DESCRIPTION OF THE PREFERRED EMBODIMENT(S)

Referring now to FIG. 1, there is illustrated therein a side elevational view of a clean breath wand 10 constructed according to the teachings of the present invention. As shown, the clean breath wand 10 includes a handle portion 12 having elongate ribs 14 thereon to facilitate gripping of the handle portion 12. These ribs 14 are also shown in section in FIG. 3.

At a proximal end 16 of the clean breath wand 10 is a coupling member 18 which, in the illustrated embodiment, is an elastomeric or rubber coupling member 18 which is received over the proximal end 16 of the clean breath wand 10 at one end and which is fitted over or fixed to a distal end 20 of a hose 22 at its other end.

As shown, above the handle portion 12 is a button member 24 which can be spring biased and which is adapted to be squeezed into a hollow body portion 26 of the wand 10 for squeezing a flexible tubing 30 inside the hollow body portion 26 of the wand 10.

It will be understood that the flexible tubing 30 is coupled to the hose 22. This can be achieved by fixing the outer periphery at a proximal end of the tubing 30 to the interior wall surface 32 (FIG. 3) of the hollow body portion 26 of the wand 10.

By applying pressure to the button member 24, the user of the wand 10 can throttle or stop the dispensing of liquid from a head end 36 of the wand 10.

As shown in FIG. 1, a distal end 38 of the tubing 30 is in communication with a back side 38 of the head end 36. As shown in FIG. 2A, the head end 36 has an outer end face 40 with openings 42 through which an irrigating and flushing liquid can be dispensed. Also as shown in FIGS. 1 and 2A three scraping ridges, ribs or blades 51–53 are provided on the outer end face 40 for scraping the tongue of a user. As shown in FIG. 2A two rows of three openings 54 and two openings 55 are located beneath the blade 53.

It will be understood that different shapes of the head end 36 can be provided, such as a generally square shaped head end as shown in FIGS. 2A–2E, a triangular shaped head end or an oblong T shaped head end, whereby the clean breath wand 10 looks something like a shaving safety razor unit.

Also, and as shown in FIGS. 2A–2E, the outer end face 40 of the head end 36 of the wand 10 can have various configurations of irrigating holes and scraping ribs or blades.

Figure 2B:
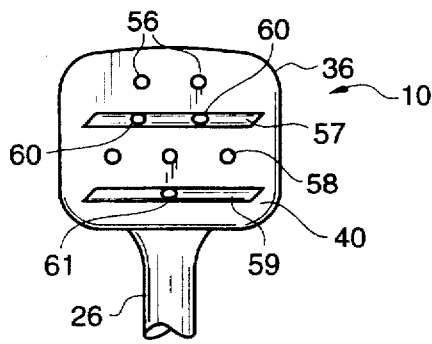

Thus, as shown in FIG. 2B, the outer end face 40 can have a first row of two irrigating openings 56, a second row having a first scraping blade 57, a third row having three irrigating openings 58, and a fourth row having a second scraping blade 59. In addition or as an alternative, two openings 60 can be provided in the blade 57 and one opening 61 in the blade 59. Further the ribs or blades 57, 59 can be rounded as shown in FIG. 1 or have an edge or a rounded edge. As a further alternative, the holes 60, 61 can be provided in a side wall of each blade 57, 59.

Figure 2C:
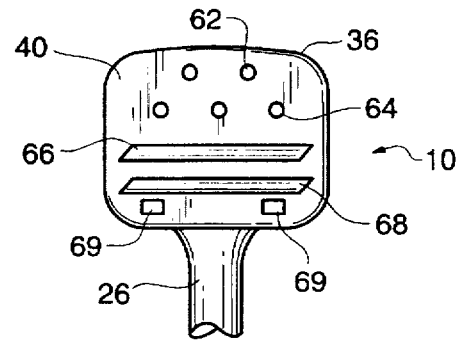

Then, in FIG. 2C another configuration of the end face 40 is shown which includes a first row of two irrigating openings 62, a second row of three irrigating openings 64 with two scraping blades 66 and 68 below the two rows of openings. Additionally, vent holes 69 can be provided through the head end 36 above or below the scraping blades 66, 68 and irrigating openings 62, 64 and are shown below the blade 68.

Figure 2D:
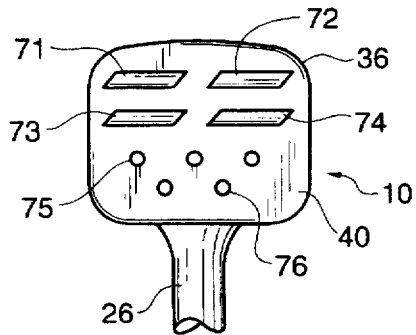

Still another configuration of the end face 40 is shown in FIG. 2D and includes two scraping blades 71–74 in a first row and a second row with three irrigating openings 75 in a third row and two irrigating openings 76 in a fourth row.

Figure 2E:
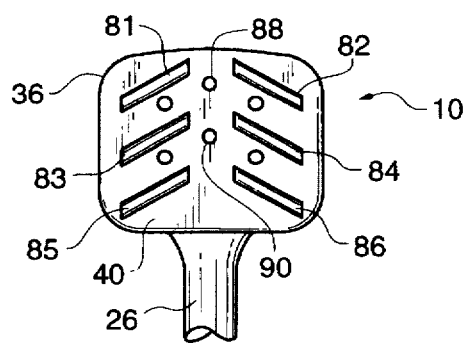

Finally, a further configuration of the end face 40 is shown in FIG. 2E and includes three pairs of scraping blades 81–86, each pair being arranged in a generally V configuration with three irrigating openings 88 in a V configuration between the first and second pairs of scraping blades 81–84, and three irrigating openings 90 in a V configuration positioned between the second and third pair of blades 83–86.

FIG. 3 illustrates a cross-section of the handle portion 12 of the wand 10 where six elongate gripping ribs 14 are provided on an outer surface 92 of the handle portion 12 which has a hollow interior 94 defined by the interior wall surface 32 in which is received the tubing 30.

FIG. 4 illustrates a connection of a proximal end 100 of the hose 22 to a source of liquid or medicant, such as to a pump of an oral irrigator device 102. As shown, the hose 22 extends from the oral irrigator device 102 to the coupling member 18 which is connected to the proximal end 16 of the wand 10.

In some instances it may be desirable to use tap water in which case the hose 22 has a cone shaped coupling member 104 at its proximal end 100 adapted to be fitted over the end of a conventional faucet 106, as shown in FIG. 5.

In FIG. 6 there is illustrated a portable clean breath wand assembly 108 which includes the wand 10 connected by the hose 22 to a squeezeable bulb 110 releasably connected to the proximal end 100 of the hose 22. The bulb 110 can be disconnected with or without the hose 22 attached from the wand 10 so that the bulb 110 can be refilled with a medicant or a breath freshener liquid.

The squeezeable bulb 110 serves as a reservoir for a medicant or breath freshener liquid.

Finally, in FIG. 7 is shown another portable clean breath wand assembly 120 which includes the wand 10, the hose 22 and a bellows type bladder 122 connected to the proximal end 100 of the hose 22, as shown in FIG. 6. Again, the bellows shaped bladder 122 can be disconnected from the wand 10 with or without the hose 22 attached for refilling of the bellows shaped bladder 122 with a medicant or breath freshener liquid.

Still other modifications of the clean breath wand 10 are shown in FIGS. 8, 9 and 10. FIG. 8 shows still another configuration of the end face 40 where there is provided an arcuate shaped blade or rib 130, arcuate in the long direction of the blade or rib 130, an irrigating opening 131 in the center of the arc and a row of two irrigating openings 132, 133 below the center opening 131 so as to form an upside down "funny face".

FIG. 9 illustrates another construction of the head end 36. In this embodiment, at least one blade or rib 140 extends downwardly from the end face 40 in an arcuate manner, such as in a partial circle or in a rounded corner frusto conical shape. A partial circular shape is shown.

FIG. 10 illustrates still another construction of the head end 36. In this embodiment, at least one blade or rib 150 extends downwardly from the end face 40 in a generally U-shaped configuration with an inverted arc 152 in the middle of the blade or rib 150.

From the foregoing description, it will be apparent that the clean breath wand 10 of the present invention has a number of advantages, some of which have been described above and others of which are inherent in the invention. Also it will be understood that modifications can be made to the clean breath wand 10 described above without departing from the teachings of the invention.

We claim:

1. A clean breath wand comprising an elongate hollow body having a distal end, a proximal end and a proximal handle portion, coupling means for coupling said proximal handle portion to a source of liquid which is pressurized, a head end fixed to said distal end of said hollow body, and said head end having an upper distal end, a lower proximal end and an outer end face, at least one irrigating opening fluidly coupled to the hollow interior of said handle portion, extending through said front end adjacent said proximal end and opening onto said outer end face, at least one tongue scraping rib or blade thereon on said outer end face, extending transversely of said outer end face with at least the ends of said at least one rib being curved or inclined toward said elongate hollow body (FIG. 8) and being located above said at least one opening and adjacent said distal end so that said rib prevents pressurized liquid from being directed posteriorly toward a users throat and liquid flow valve means for controlling the delivery of pressurized liquid to said at least one opening.

2. The clean breath wand of claim 1 wherein said outer end face has at least two spaced apart scraping ribs therein and at least three irrigating openings extending through said front end.

3. The clean breath wand of claim 1 wherein said end face has at least five irrigating openings extending therethrough and at least two spaced apart scraping blades on said outer end face.

4. The clean breath wand of claim 1 wherein said end face has six scraping ribs thereon with six spaced irrigating openings extending through said head end.

5. The clean breath wand of claim 1 wherein said at least one blade has a rounded cross-section.

6. The clean breath wand of claim 1 wherein said at least one blade has an outer scraping edge.

7. The clean breath wand of claim 1 wherein said valve means include a movable button member mounted on an underside of said hollow body and engageable by a finger of the user, said hollow body having a tubing therein communicating between the liquid source and an inside back side of said head end, said tubing being engageable by said button when it is squeezed by a user to throttle or stop the flow of liquid from the liquid source through the tubing to said outer end face of said head end of said clean breath wand.

8. The clean breath wand of claim 1 wherein said handle portion of said body has elongate ribs thereon to facilitate gripping of the wand.

9. The clean breath wand of claim 1 wherein said coupling means include a hose extending to the source of liquid.

10. The clean breath wand of claim 9 wherein said coupling means include an elastomeric collar adapted to engage said proximal end of said wand and a distal end of said hose leading to the source of liquid.

11. The clean breath wand of claim 9 wherein said hose is connectable to a liquid pumping device.

12. The clean breath wand of claim 9 wherein said hose is connected to a coupling member adapted to be connected to a faucet.

13. The clean breath wand of claim 1 wherein said outer end face has at least one arcuate shaped blade or rib, being arcuate in the long direction of the blade or rib (130 in FIG. 8).

14. The clean breath wand of claim 13 wherein said outer end face has one irrigating opening in the center of the arc so as to form an upside down "funny face".

15. The clean breath wand of claim 14 wherein said outer end face has a row of two irrigating openings below the center opening so as to form better an upside down "funny face".

16. The clean breath wand of claim 1 wherein said outer end face has at least one blade or rib that extends downwardly from the end face in an arcuate manner, such as in a partial circle or in a rounded corner shape (FIG. 9).

17. The clean breath wand of claim 1 combined with a pump having a reservoir and the output from said pump being directly coupled to the hollow interior of said handle portion.

18. A clean breath wand comprising an elongate hollow body having a distal end, a proximal end and a proximal handle portion, coupling means for coupling said proximal handle portion to a source of liquid which is capable of being placed under pressure, a head end fixed to said distal end of said hollow body, and said head end having an upper distal end, a lower proximal end and an outer end face, at least one irrigating opening fluidly coupled to the hollow interior of said handle portion, extending through said front end adjacent said proximal end and opening onto said outer end face, at least one tongue scraping rib or blade thereon on said outer end face, extending transversely of said outer end face with at least the ends of said at least one rib being curved or inclined toward said elongate hollow body (FIG. 8) and being located above said at least one opening and adjacent said distal end so that said rib prevents pressurized liquid from being directed posteriorly toward a users throat and liquid flow valve means for controlling the delivery of pressurized liquid to said at least one opening.

* * * * *